United States Patent
Burtt

(10) Patent No.: US 11,230,612 B2
(45) Date of Patent: Jan. 25, 2022

(54) KITS AND METHODS OF USING HYALURONIDASE TO MODIFY POLYSACCHARIDE FILLERS AND DELIVERY SYSTEMS

(71) Applicant: Advanced Aesthetic Technologies, Inc., Brookline, MA (US)

(72) Inventor: Richard Burtt, Charlestown, MA (US)

(73) Assignee: Advanced Aesthetic Technologies, Inc., Brookline, MA (US)

( * ) Notice: Subject to any disclaimer, the term of this patent is extended or adjusted under 35 U.S.C. 154(b) by 101 days.

(21) Appl. No.: 16/486,697

(22) PCT Filed: Feb. 16, 2018

(86) PCT No.: PCT/US2018/000039
§ 371 (c)(1),
(2) Date: Aug. 16, 2019

(87) PCT Pub. No.: WO2018/151827
PCT Pub. Date: Aug. 23, 2018

(65) Prior Publication Data
US 2020/0010577 A1   Jan. 9, 2020

Related U.S. Application Data

(60) Provisional application No. 62/460,756, filed on Feb. 18, 2017.

(51) Int. Cl.
| | | |
|---|---|---|
| C08B 37/00 | (2006.01) | |
| A61K 47/36 | (2006.01) | |
| A61K 8/66 | (2006.01) | |
| A61K 8/73 | (2006.01) | |
| A61Q 19/08 | (2006.01) | |

(52) U.S. Cl.
CPC ............ *C08B 37/0039* (2013.01); *A61K 8/66* (2013.01); *A61K 8/735* (2013.01); *A61K 47/36* (2013.01); *A61Q 19/08* (2013.01); *C12Y 302/01035* (2013.01)

(58) Field of Classification Search
CPC .... C08B 37/0039; A61K 8/735; A61K 47/36; A61K 8/66; A61Q 19/08; C12Y 302/01035
USPC .......................................................... 514/53
See application file for complete search history.

(56) References Cited

U.S. PATENT DOCUMENTS

| | | |
|---|---|---|
| 2010/0239635 A1 | 9/2010 | McClain et al. |
| 2013/0203696 A1 | 8/2013 | Njikang et al. |
| 2014/0328826 A1 | 11/2014 | Cole |
| 2016/0038635 A1 | 2/2016 | Matteuzzi |

FOREIGN PATENT DOCUMENTS

| | | |
|---|---|---|
| FR | 2374040 A1 | 7/1978 |
| JP | 2009-102279 A | 5/2009 |
| WO | 2014/077575 A1 | 5/2014 |
| WO | 2016/100476 A1 | 6/2016 |
| WO | 2016/154277 A1 | 9/2016 |

OTHER PUBLICATIONS

Bean et al. Triggered Release of Bacteriophage K from Agarose/Hyaluronan Hydrogel Matrixes by *Staphylococcus aureus* Virulence Factors. Chem. Mater. 2014, 26, 7201-7208. (Year: 2014).*
International Search Report and Written Opinion for Application No. PCT/US2018/000039, dated May 1, 2018, 8 pages.

* cited by examiner

*Primary Examiner* — Yih-Horng Shiao
(74) *Attorney, Agent, or Firm* — McCarter & English, LLP; Michael J. DeGrazia; Mei Bai

(57) ABSTRACT

Embodiments of the present invention are directed to kits, compositions and methods for modifying and altering polysaccharide fillers and drug delivery systems with the application of hyaluronidase.

7 Claims, 5 Drawing Sheets

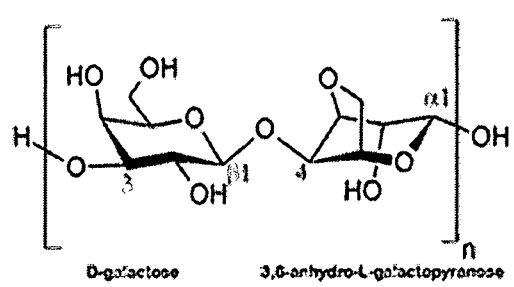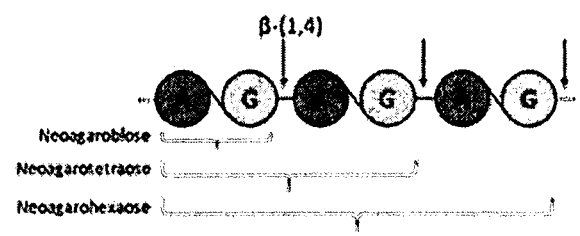
*Fig. 2A*  *Fig. 2B*

KITS AND METHODS OF USING HYALURONIDASE TO MODIFY POLYSACCHARIDE FILLERS AND DELIVERY SYSTEMS

RELATED APPLICATION INFORMATION

This application is a § 371 of International Patent Application No.: PCT/US2018/000039, filed Feb. 16, 2018, which claims priority to U.S. Provisional Application Ser. No.: 62/460,756, filed on Feb. 18, 2017. The entire contents of the aforementioned applications are incorporated herein by reference.

STATEMENT REGARDING FEDERAL FUNDING

Embodiments of the present invention were not conceived or reduced to practice with Federal sponsorship.

BACKGROUND OF THE INVENTION

Polysaccharides are used as cosmetic fillers and as a component of injectable drug delivery systems. When polysaccharides are placed in the body as a filler or as a drug delivery system, the polysaccharides may have a long period of time before such are resorbed into the body through metabolism or other means.

Polysaccharides used as fillers have certain properties such as viscosity, resistance to degradation, texture, feel, resistance to pressure and the like. These properties are dictated by the organisms from which the polysaccharides are derived or isolated from.

SUMMARY OF THE INVENTION

Embodiments of the present invention facilitate the use of polysaccharides, particularly as such polysaccharides are used as fillers and drug delivery vehicles. Embodiments of the present invention allow the polysaccharide to be modified in vivo or in vitro to impart special physical and chemical properties. For example, without limitation, the physical properties of texture, feel, resistance to pressure, viscosity and the like can be altered or modified, in vivo or in vitro. Similarly, the chemical properties, resistance to degradation and speed, of degradation can be modified or altered.

The modification of physical and chemical features of a polysaccharide used as a filler or drug delivery system allows the health practitioner to modify the filler mass after it has been placed in the body or prior to placement in the body. As used herein, the term, "mass" refers to the polysaccharide material and the surrounding space it occupies. For example, polysaccharide fillers used for cosmetic purposes typically comprise solutions of 1.0 to 5.0%. These solutions may also comprise other materials to improve the flow or feel of the filler, such as hyaluronic acid, and anesthetic agents to address the potential discomfort during the administration of the filler. Anesthetic agents are well known in the art and include, without limitation, lidocaine. These fillers are administered to the deep layer of the skin. An example of a filler of this type is described in PCT/IB2014/060322 to Ghimas SPA, the entire content of which is incorporated herein by reference.

One embodiment of the present invention is directed to a method of altering or modifying a mass comprising a polysaccharide held in the body of an animal. The method comprises the steps of administering an effective amount of hyaluronidase to the mass. The hyaluronidase can be administered to the mass prior to the mass being placed in the body or after the mass has been placed in the body.

One embodiment of the method features a polysaccharide having one or more sugars selected from the group consisting of D-galactose and 3,6-anhydro-L-galactopyranose. These sugars are the constituents of agarose. Agarose is used as a dermal filler and as a drug delivery vehicle. As used herein, a "drug delivery vehicle" comprises a polysaccharide and one or more drugs.

As used herein, the term "hyaluronidase" refers to an enzyme which cleave Beta-1,4 bond of hyaluronic acid. The term hyaluronidase includes its salts and derivatives which retain its enzymatic activity. A recombinant form of hyaluronidase for human injection, sold under the trademark Hylenex® (Halozyme, Inc., San Diego, Calif.), is an FDA approved enzyme, and the current standard for the off-label use of treating overcorrection of hyaluronic acid (HA) based dermal fillers. Hyaluronidase hydrolyzes HA by cleaving the $\beta$-1,4 bond between the glucosamine and glucuronic acid.

Surprising and unexpectedly, hyaluronidase alters the form of the polysaccharide, increasing its dissolution, breaking down and fluidizing the mass. It is surprising and unexpected because enzymes such as hyaluronidase are highly specific in the substrate. The polysaccharide having one or more sugars selected from the group consisting of D-galactose and 3,6-anhydro-L-galactopyranose, such as agarose is one such polysaccharide to which hyaluronidase acts upon. As used herein, the term "an effective amount" refers to an amount to cause the polysaccharide to assume a desired fluidized form. The desired fluidized form refers to a more fluid form compared to agarose of same polymer composition and hydration without a hyaluronidase being present.

Wherein the mass is a delivery vehicle for one or more drugs, the hyaluronidase has utility to facilitate removal of the polysaccharide, control the delivery or release of drug, address hardness, graininess or nodules in the mass and minimize the mark on the skin from the injection of drug. For example, without limitation, one embodiment of an invention directed to a drug delivery system comprises a polysaccharide and hyaluronidase held in a vessel for reconstitution. Upon reconstitution, the hyaluronidase is injected into a mass of the polysaccharide to act on the polysaccharide and render the polysaccharide in a more fluid state.

As used herein, the term "drug" is used to refer to any compound or compounds used to effect a biological change or treat a medical condition. The drug may be incorporated into the polysaccharide prior to reconstitution or after reconstitution. Examples of drugs include without limitation, lidocaine, and other anesthetic agents, onabotulinemtoxin A (BOTOX®, Allergan) and other aesthetic agents.

A further embodiment of the present invention is directed to a kit for performing dermal filling procedures or for the administration of drug. The kit comprises a polysaccharide for forming a mass in the body of an animal and a hyaluronidase for maintaining or making the polysaccharide more fluid for administration to the mass held in the body to effect a modification, correction or speeding the resorption of the mass.

One embodiment of the present kit features a polysaccharide having one or more sugars selected from the group consisting of D-galactose and 3,6-anhydro-L-galactopyranose. These sugars are constituents of the polysaccharide, agarose.

A further embodiment of the present invention is directed to a formulation for a dermal filler. The formulation comprises the reaction product of agarose and hyaluronidase. One reaction product is neoagarohexaose. One formulation comprises agarose and neoagarohexaose. Neoagarohexarose is added to agarose to create a dermal filler or drug delivery vehicle with properties of desire texture, viscosity, injectability and resistance to degradation.

These and other features and advantages will be apparent to those skilled in the art upon viewing the figure which is briefly described below and studying the details description that follows.

BRIEF DESCRIPTION OF THE DRAWINGS

FIG. 2A shows the structure of agarose;

FIG. 2B illustrates cleavages on agarose, having features of the present invention;

DETAILED DESCRIPTION OF THE INVENTION

Embodiments of the present invention will now be described in detail with respect to a kit for performing dermal filling procedures or for the administration of drug. The present description is directed to embodiments which are considered to be the best mode to practice the present invention at the time of the writing of the present description. Those skilled in the art will recognize that the understanding of the best mode may change in time. Those skilled in the art will also recognize that the features of the present invention described are subject to alteration and modification and such that the present discussion should not be considered limiting.

Figure 1:
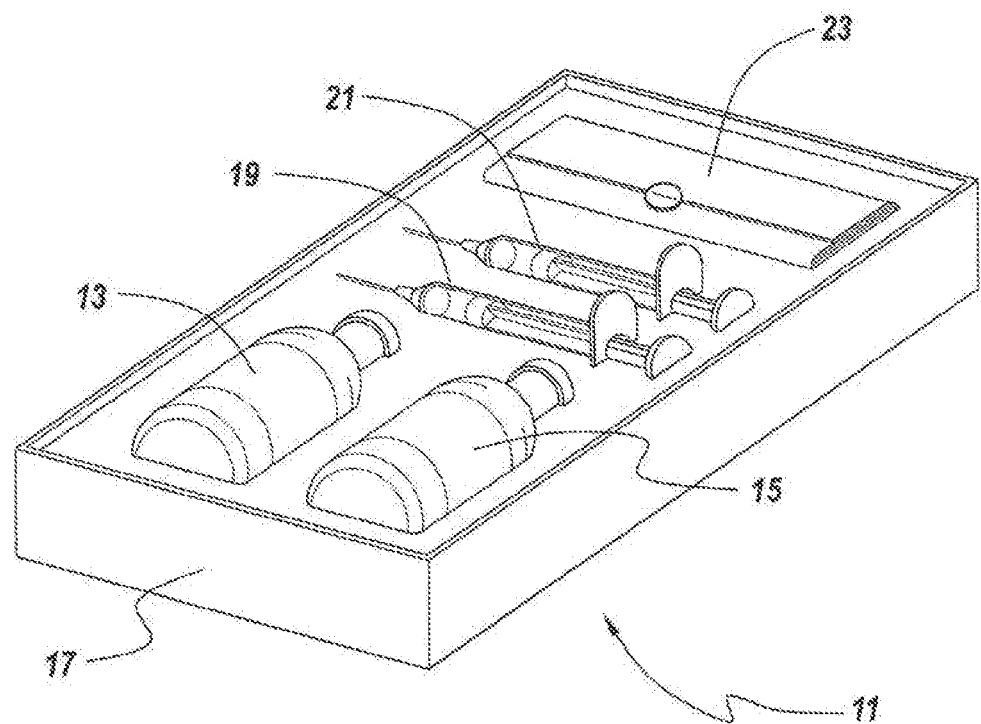
FIG. 1 depicts a kit embodying features of the present invention.

Turning now to FIG. 1, a kit, generally designated by the numeral 11, embodying features of the present invention is depicted. The term "kit" is used to denote a bundled assembly of parts and constituents for performing a method. The kit 11 comprises two vials, a first vial 13 containing a polysaccharide for forming a mass in the body of an animal and a second vial 15 containing hyaluronidase for fluidizing the polysaccharide for administration to the mass held in the body. The first vial 13 and second vial 15 are bundled or held in a package 17 with means for administering the polysaccharide and means for administering the enzyme, in the form of first syringe 19 and second syringe 21, and instructions 23.

The first vial 13 contains a polysaccharide for forming a mass in the body of an animal or patient. The polysaccharide can be pre-made and in a final form ready for administration or be lyophilized for reconstitution with water. The first syringe 19 is used to withdraw the reconstituted or pre-made polysaccharide for injection into an animal or patient. For example, a human subject may use the mass to conceal wrinkles or to build bulk to areas of the body showing signs of atrophy or for which a fuller appearance is desired.

The present kit features a polysaccharide having one or more sugars selected from the group consisting of D-galactose and 3,6-anhydro-L-galactopyranose. These sugars are constituents of the polysaccharide, agarose, which is used as a dermal filler. Agarose is sold as a dermal filler under the mark ALGINESS®.

The second vial 15 contains hyaluronidase to effect a modification or speeding the resorption or altering the fluidity of the mass. The hyaluronidase can be pre-made and in a final form ready for administration or be lyophilized for reconstitution with water. The second syringe 21 is used to withdraw the reconstituted or pre-made hyaluronidase for injection into the mass. For example, in a human subject using the mass to conceal wrinkles or to build bulk to areas of the body showing signs of atrophy, the subject may desire the mass to have a softer feel, or the mass may exhibit graininess or nodules or the mass may have been overinjected. As used herein the term, "overinjected" refers to a condition in which the mass appears too large for the desired effect. The hyaluronidase is placed in the mass and the mass manipulated to distribute the hyaluronidase where the hyaluronidase may effect a modification of the polysaccharide. The polysaccharide assumes a more fluid form, capable of faster metabolization, removing graininess and nodules and presenting a softer mass and/or a mass which is reduced or will be reduced in size more quickly.

Embodiments of the present invention facilitate the use of polysaccharides, particularly as such polysaccharides are used as fillers and drug delivery vehicles. Embodiments of the present invention allow the polysaccharide to be modified in vivo or in vitro to impart special physical and chemical properties. That is, the hyaluronidase can be distributed into the polysaccharide prior to administration of the polysaccharide or after administration of the polysaccharide to create a desired physical property of texture, feel, resistance to pressure, viscosity and the like. Similarly, the chemical properties of resistance to degradation and speed of degradation can be modified or altered.

The modification of physical and chemical features of a polysaccharide used as a filler or drug delivery system allows the health practitioner to modify the filler mass after it has been placed in the body or prior to placement in the body. For example, the mass may be fluidized for removal or minimization by withdrawing the mass after the administration of the hyaluronidase. The fluidization of the mass allows the mass to be redistributed and aids in the resorption of the mass.

The use of the kit 11 and the instructions 23 will now be described with respect to an embodiment of the present invention directed to a method of altering or modifying a mass comprising a polysaccharide held in the body of an animal. The instructions 23 direct the user to reconstitute the polysaccharide held in first vial 13 and the hyaluronidase held in second vial 15 if reconstitution is needed. The instructions 23 direct the user to administer polysaccharide held in the first vial 13. The instructions 23 further direct the user to administer an effective amount of hyaluronidase for the polysaccharide to the mass. The hyaluronidase can be administered to the mass prior to the mass being placed in the body or after the mass has been placed in the body. More than one application of hyaluronidase may be used to obtain the desired consistency of the mass. The mass may be gently kneaded or manipulated to distribute the hyaluronidase throughout the mass structure. The fluidized mass may be manipulated into a desired position or removed by suction through the same syringe administering the hyaluronidase.

Embodiments of the method and kits feature a polysaccharide having one or more sugars selected from the group consisting of D-galactose and 3,6-anhydro-L-galactopyranose. These sugars are the constituents of agarose. Agarose is used as a dermal filler and as a drug delivery vehicle.

Embodiments of the method and kits features hyaluronidase. Hyaluronidase is well tolerated and the amount is based on the mass of polysaccharide. Monographs, for such enzyme, are available from the respective manufacturers and are incorporated herein by reference.

A further embodiment of the present invention is directed to a formulation for a dermal filler. The formulation comprises the reaction product of agarose and hyaluronidase with agarose. One reaction product is neoagarohexaose. One formulation comprises agarose and neoagarohexarose. Neoagarohexarose is added to agarose to create a dermal filler or drug delivery vehicle with properties of desire texture, viscosity, injectability and resistance to degradation.

The relative percentages of agarose and neoagarosehexaose are chosen for the desired texture, viscosity, injectability and resistance to degradation. For example, without limitation, formulations with higher percentages of neoagarosehexaose and lower percentages of agarose may show higher rates of resorption in the body, greater injectibility, lower viscosity and smoother texture. One embodiment of the present formulation comprises a range of 99-50% agarose with the remainder neoagarosehexaose, another embodiment features 95-75% agarose with the remainder neoagarosehexaose, and another embodiment features 99-90% agarose and the remainder neoagarosehexaose.

These and other features will be apparent form the following Example.

EXAMPLE

Methods: First, pure agarose was exposed to Hylenex® recombinant (hyaluronidase human injection) and β-agarase. Liquid chromatography/mass spectrometry (LC/MS) was used to detect the presence of oligosaccharides which are known breakdown products of agarose. Finally, the effects of hyaluronidase and β-agarase were compared on Algeness® dermal fillers.

Results: Hylenex® recombinant (hyaluronidase human injection) is the so-called gold standard for treating over-injection or negative side-effects of hyaluronic acid dermal fillers. Hyaluronidase cleaves the β-1,4 linkage of hyaluronic acid. While the structure of hyaluronic acid and agarose are very different, it is possible for hyaluronidase to hydrolyze agarose at the β-1,4 bond. As expected, β-agarase cleaved agarose at the β-1,4 glyosidic linkages producing the dimer, tetramer and hexamer neoagaro oligosaccharides. The presence of the hexamer was also observed in the agarose sample exposed to Hylenex®.

Conclusions: The enzymatic hydrolysis of pure agarose by β-agarase produced three compounds, neoagarobiose, neoagarotetraose and neoagarohexaose, which result from the cleavage of β-1,4 glycosidic bonds. The enzymatic hydrolysis of agarose by Hylenex® produced one product, neoagarohexaose. Similar results were observed in the enzymatic degradation of Algeness® DF when exposed to β-agarase and Hylenex®.

As shown in FIG. 2A, agarose is linear polymer composed of repeating units of D-galactose and 3,6-anhydro-L-galactopyranose, linked by α-1,3 and β-1,4 glycosidic bonds. FIG. 2B shows that β-agarase hydrolyzes by cleaving agarose at the β-1,4 bond between D-galactose (G) and 3,6-anhydro-L-galactopyranose (A), producing a series of neoagarooligosaccharides with repeating disaccharide units.[1] Depending on the cleavage site, neoagarooligosaccharides of varying molecular mass can be produced, including neoagarobiose (324.28 g/mol), neoagarotetraose (630.55 g/mol) and neoagarohexaose (936.82 g/mol).

Figure 3:
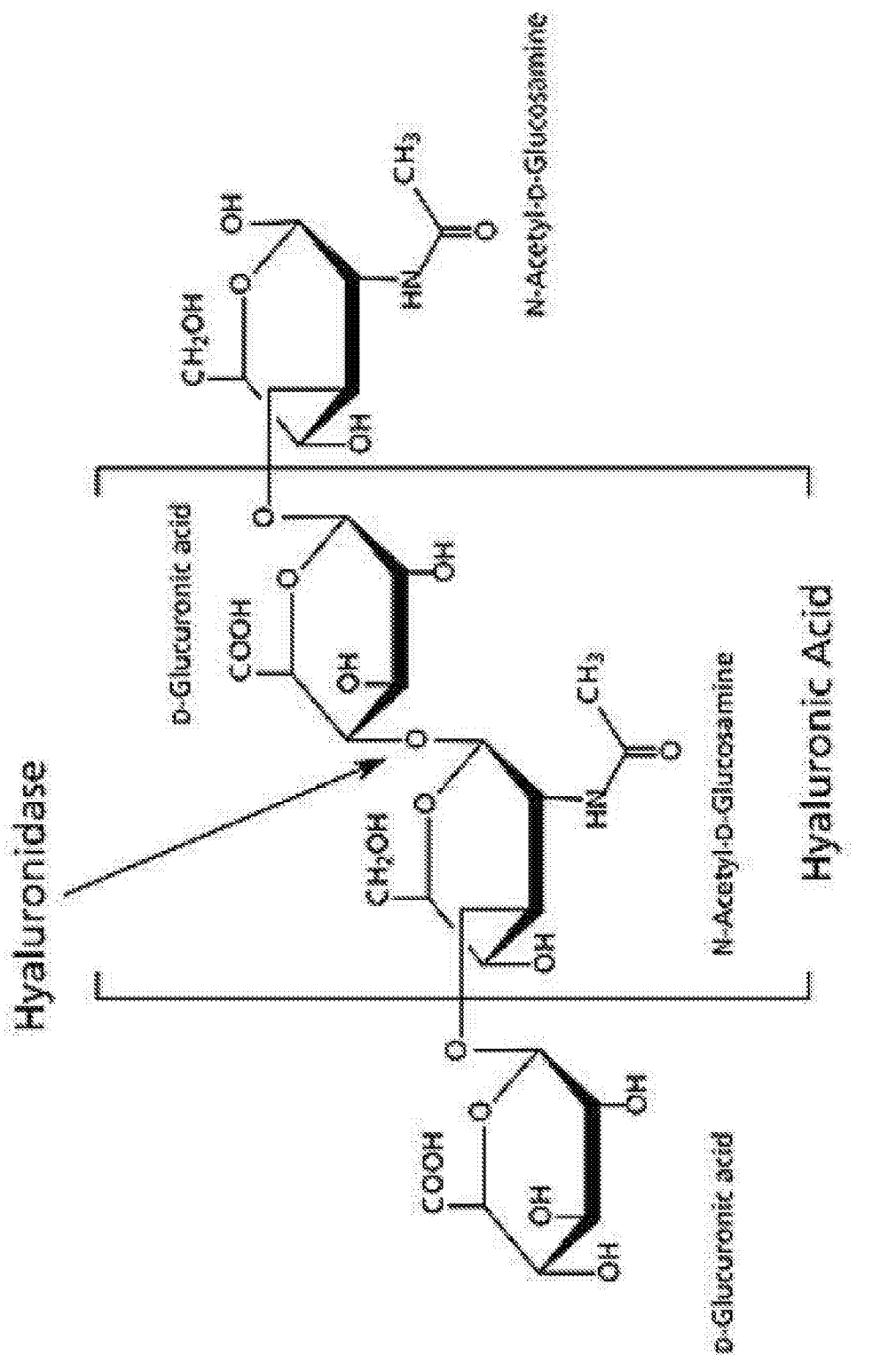
FIG. 3 is an image showing a cleavage on HA.

Hylenex® recombinant (hyaluronidase human injection) is an FDA approved enzyme, and current standard for the off-label use of treating overcorrection of hyaluronic acid (HA) based dermal fillers.[2-4] HA is composed of repeating units of N-Acetyl-D-Glucosamine and D-Glucuronic acid, linked by β-1,3 and β-1,4 bonds. Hyaluronidase hydrolyzes HA by cleaving the β-1,4 bond between the glucosamine and glucuronic acid, producing a series of repeating disaccharide units, as shown in FIG. 3 (Image from: www.sigmaaldrich.com).

The objective of this study was to determine if Hylenex® recombinant hydrolyzes the agarose-based dermal filler, Algeness® DF, based on the cleavage of the β-1,4 linkage D-galactose and 3,6-anhydro-L-galactopyranose. Neoagarotetraose was used as a reference standard to confirm enzymatic activity in this study.

Experimental

Control Samples—0.2% Agarose Gel

Agarose powder (0.2 g) was added to 100 ml of water (99° C.) and cooled in a water bath to 42° C. Three control samples were prepared using 1000 µl of molten agarose (2 mg). Samples were incubated at 42° C. for 2 hours, and then either 1) centrifuged at 3000 g for 5 min at 4° C., 2) centrifuged at 12000 g for 5 min at 4° C. or 3) heated at 90° C. for 10 minutes ("kill enzyme" step) and centrifuged at 12000 g for 5 min at 4° C. Supernatant was filtered using 0.2 µm Nylon membrane filters. All samples were analyzed by LC/MS to determine if sample preparation methods degraded the agarose gel. Additionally, the Molisch test for sugars was conducted on all samples.

Enzyme Degradation—0.2% Agarose Gel

Agarose gel (0.2%) was exposed to Hylenex® recombinant (hyaluronidase human injection) and β-agarase to compare the effects of enzymatic degradation on the two samples. Briefly, Hylenex® (200 µl—30 units) was added to agarose (200 µl—0.4 mg agarose) and incubated at 37° C. for 2 hours. Additionally, β-agarase (5 µl—5 units) was added to agarose (1000 µl—2 mg agarose) and incubated at 37° C. for 2 hours. Samples were centrifuged at 12000 g for 5 min at 4° C. The supernatant was filtered using 0.2 µm Nylon membrane filters and analyzed by LC/MS. Additionally, the Molisch test for sugars was conducted on all samples.

Enzyme Degradation—Algeness® DF and Juvederm® Ultra Plus XC

Algeness® DF (3.5% agarose) and Juvederm® Ultra Plus XC (2.4% HA) were exposed to Hylenex® recombinant (hyaluronidase human injection) to compare the effects of enzymatic degradation. In addition, Algeness® DF was exposed to β-agarase for comparison. Briefly, enzyme was added to the dermal filler and stirred (800 rpm) at room temperature for 6 hours. Table 1 shows the amount of dermal filler and enzyme used for each reaction. After the reaction, samples were heated at 90° C. for 10 minutes ("kill enzyme") and then centrifuged at 10000 g for 5 min at 4° C. Supernatant was filtered using 0.2 µm Nylon membrane filters and analyzed by LC/MS. Additionally, the Molisch test for sugars was conducted on all samples.

TABLE 1

| Sample | Vol. Algeness ® | Vol. Juvederm ® | Vol. Hylenex ® | Vol. β-agarase |
|---|---|---|---|---|
| AA | 200 µl - 7 mg Agarose | — | — | 200 µl - 200 units |
| AH | 700 µl - 24.5 mg Agarose | — | 700 µl - 105 units | — |
| JH | — | 400 µl - 9.6 mg HA | 400 µl - 60 units | — |

In Table 1 above, the designations "AA", "AH" and "JH" refer respectively to Algeness ®/β-agarase, Algeness ®/Hylenex ® and Juvederm ®/Hylenex ® (control)

LC/MS

Separations were performed on an Agilent 1260 LC/MS equipped with a cooled autosampler tray (4° C.) and temperature-controlled column compartment (20° C.), which held a 2.1×100 mm i.d., 3.5 µm particle size $C_{18}$ Zorbax Eclipse Plus column (Agilent, Santa Clara, Calif.). Sample injection volumes were 5 uL. A gradient elution was employed with a mobile phase composition of 0.5 mM ammonium acetate in 18Ω Millipore water (A) and acetonitrile (B), and flow rate of 0.4 mL/min. The gradient profile is shown in Table 2.

TABLE 2

| Time (min) | % A | % B |
|---|---|---|
| 0.5 | 100.0 | 0.0 |
| 5 | 2.0 | 98.0 |
| 6 | 2.0 | 98.0 |
| 7 | 100.0 | 0.0 |
| 8 | 100.0 | 0.0 |

The MS was operated in positive ionization mode for agarose and negative ionization mode for hyaluronic acid, with a fragmentation voltage of 100V. Spectra were recorded in full scan mode from 300 to 2000 m/z. Neoagarotetraose, a known degradation product of agarose when exposed to β-agarase, was used to confirm enzyme activity.

Experimental (In Progress)

Enzyme Degradation—3.5% Agarose Gel

Agarose gel (3.5%) was exposed to Hylenex® recombinant (hyaluronidase human injection) and β-agarase to compare the effects of enzymatic degradation. Briefly, Hylenex® (200 µl—30 units) was added to agarose (400 µl—14 mg agarose) and incubated at 37° C. for 2 hours. Additionally, β-agarase (30 µl—30 units) was added to agarose (400 µl—14 mg agarose) and incubated at 37° C. for 2 hours. Samples were centrifuged at 10000 g for 5 min at 4° C. Supernatant was filtered using 0.2 µm Nylon membrane filters and analyzed by LC/MS. Additionally, the Molisch test was conducted on all samples.

Enzyme Degradation—Algeness® DF and Juvederm® Ultra Plus XC

Algeness® DF (3.5% agarose) and Juvederm® Ultra Plus XC (2.4% HA) were exposed to Hylenex® recombinant (hyaluronidase human injection) to compare the effects of enzymatic degradation. In addition, Algeness® DF was also exposed to β-agarase for comparison. Briefly, enzyme was added to the dermal filler and incubated at 37° C. for 48 hours. Table 3 shows the amount of dermal filler and enzyme used for each reaction. After incubation period, samples were heated at 90° C. for 10 minutes ("kill enzyme") and then centrifuged at 10000 g for 5 min at 4° C. Supernatant was filtered using 0.2 µm Nylon membrane filters and analyzed by LC/MS. Additionally, the Molisch test for sugars was conducted on all samples.

TABLE 3

| Sample | Vol. Algeness ® | Vol. Juvederm ® | Vol. Hylenex ® | Vol. β-agarase |
|---|---|---|---|---|
| AA | 400 µl-14 mg Agarose | — | — | 30 µl-30 units |
| AH | 400 µl-14 mg Agarose | — | 200 µl-30 units | — |
| JH | — | 600 µl-14.4 mg HA | 200 µl-30 units | — |

In Table 3 above, the designations "AA", "AH" and "JH" refer respectively to Algeness ®/β-agarase, Algeness ®/Hylenex ® and Juvederm ®/Hylenex ® (control)

Results 0.2% Agarose Gel

Figure 4:
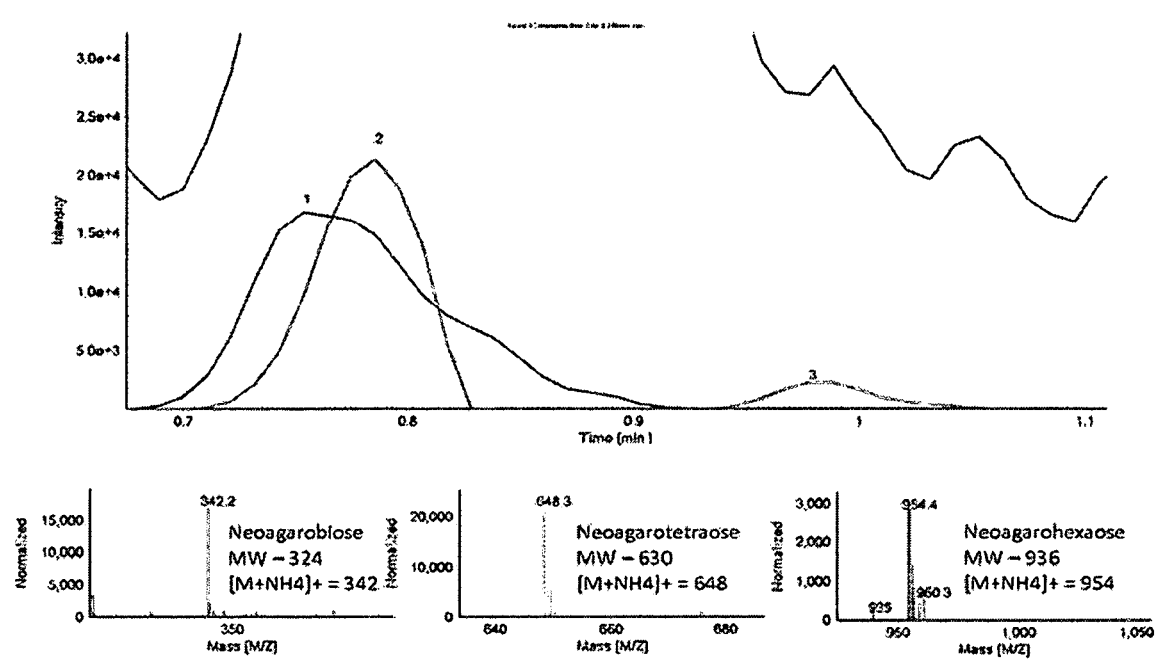
FIG. 4 is an ion chromatogram of a sample, having features of the present invention.
Figure 5:
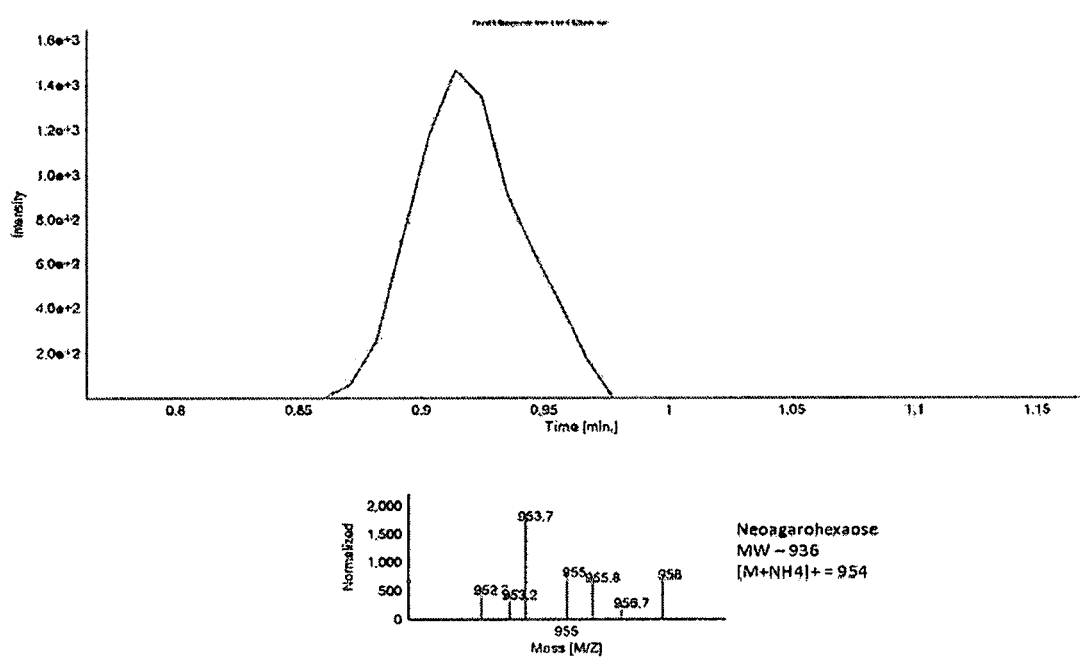
FIG. 5 is another ion chromatogram of a sample, having features of the present invention.

The analysis of pure agarose and β-agarase and Hylenex® were carried out to determine whether the enzymes hydrolyzed the starting material. After incubation, samples were analyzed by LC/MS to determine the presence of neoagarooligosaccharides, thus confirming if the enzyme produced the expected products. Neoagarotetraose was used as a reference standard. As expected, the analysis of the agarose/β-agarase sample produced three breakdown products, neoagarobiose, neoagarotetraose and neoagarohexaose, as shown in FIG. 4. FIG. 4 includes two sub-figures, the top one is an ion chromatogram for the three products represented by three peaks designated 1, 2 and 3, and the bottom one consists of three mass spectra, corresponding respectively to the three products. On the other hand, LC/MS analysis of the agarose/Hylenex® sample revealed the hexasaccharide only, as shown in FIG. 5. FIG. 5 also includes two sub-figures, the top one is an ion chromatogram for the hexasaccharide represented by a chromatographic peak, and the bottom one is a mass spectrum corresponding to the hexasaccharide. Although results are not quantitative, neoagarotetraose produced the highest signal in the agarose/β-agarase sample. The neoagarohexaose signal from the reaction of agarose/Hylenex® was buried in the sample matrix, but observable using spectral deconvolution software, at near instrument detection limits. Based on these results, Hylenex® hydrolyzes agarose, however further studies should be conducted to determine reaction speed and amount. Note: all observations are based on one analysis and should be repeated to confirm findings.

Algeness® DF and Juvederm® Ultra Plus XC

The Molisch test is a qualitative analysis used to indicate the presence of carbohydrates in a sample. A positive result is indicated by a purple ring between the sample and the concentrated acid. If sugars are not present in the sample, the solution will remain clear. The presence of monosaccharides results in a faster reaction, while disaccharides and polysaccharides will result in a slower reaction time.

The Molisch test conducted on three samples: Algeness®/β-agarase, Algeness®/Hylenex® and Algeness®/water (control), contained separately in three test tubes. Immediately upon adding the Molisch reagent to each of the test tubes, the Algeness®/β-agarase sample turned dark purple, the Algeness®/Hylenex® sample remained the same, and the control (Algeness®/water) formed a light purple ring at the interface of the sample and the concentrated acid, presumably due to acid hydrolysis. After 1 hour, the Algeness®/β-agarase and the control remained the same, while the Algeness®/Hylenex® formed a light purple ring. Finally, after 2 hours, the Algeness®/Hylenex® turned a darker shade of purple. Based on these observations, the Algeness®/β-agarase presumably has smaller chain sugars present vs. Algeness®/Hylenex®. The results of the Algeness®/Hylenex® were compared to that of the Juvederm®/Hylenex®. After 19 hours, the Juvederm®/Hylenex® produced positive results (slight purple/pink). The Juvederm® control (Control J) also showed a positive result, presumably due to acid hydrolysis. When reactions are allowed to sit, the solution may turn yellow-green as observed with the Algeness® control. These samples were also analyzed by LC/MS, yielding similar results.

Thus, the present invention has been described in detail with the understanding that the present discussion is subject to modification and alteration without departing from the teaching. Therefore, the present invention should not be limited to the precise details but should encompass the subject matter of the claims that follow and their equivalents.

The invention claimed is:

1. A method of altering or modifying a mass comprising a polysaccharide comprising the step of:
   administering an effective amount of a hyaluronidase to the mass or an effective amount of a hyaluronidase with said polysaccharide to form the mass, wherein said polysaccharide has one or more sugars selected from the group consisting of D-galactose and 3,6-anhydro-L-galactopyranose, and wherein the effective amount is obtained by an assay to detect neoagarohexaose after hyaluronidase hydrolysis.

2. The method of claim 1, wherein said hyaluronidase is a recombinant enzyme.

3. The method of claim 1, wherein said polysaccharide is an agarose.

4. The method of claim 1, wherein said mass is a dermal filler.

5. The method of claim 1, wherein said mass is a delivery vehicle for one or more drugs.

6. The method of claim 1, wherein said hyaluronidase is administered to the mass in vivo.

7. The method of claim 1, wherein said hyaluronidase is administered with the polysaccharide.

* * * * *